United States Patent [19]

Kita et al.

[11] 4,436,922
[45] Mar. 13, 1984

[54] METHOD FOR MANUFACTURE OF HIGH-PURITY PHTHALIC ANHYDRIDE

[75] Inventors: Yuichi Kita, Akashi; Kentaro Sakamoto, Hyogo; Takahisa Sato, Himeji, all of Japan

[73] Assignee: Nippon Shokubai Kagaku Kogyo Co., Ltd., Osaka, Japan

[21] Appl. No.: 394,477

[22] Filed: Jul. 1, 1982

[30] Foreign Application Priority Data

Jul. 6, 1981 [JP] Japan .................. 56-104404
Jul. 15, 1981 [JP] Japan .................. 56-109300
Nov. 7, 1981 [JP] Japan .................. 56-177808

[51] Int. Cl.$^3$ .......................... C07D 307/89
[52] U.S. Cl. ............................... 549/251
[58] Field of Search ........................ 549/251

[56] References Cited

U.S. PATENT DOCUMENTS 3,201,423  8/1965  Landau et al. .......... 549/248
4,165,324  8/1979  Schroeder et al. ....... 549/251
4,234,494  11/1980  Schroeder et al. ...... 549/251

FOREIGN PATENT DOCUMENTS 1260457  2/1968  Fed. Rep. of Germany .
1935008  1/1971  Fed. Rep. of Germany .
1302453  5/1961  France .
1600064  7/1970  France .
45-10333  4/1970  Japan .

Primary Examiner—Richard Raymond
Attorney, Agent, or Firm—Omri M. Behr

[57] ABSTRACT

A method for the manufacture of high-purity phthalic anhydride, which comprises exposing crude phthalic anhydride obtained by vapor-phase catalytic oxidation of ortho-xylene to contact with a gas containing molecular oxygen at an elevated temperature in the presence of an alkali metal salt of at least one carboxylic acid selected from the group consisting of maleic acid, succinic acid and benzoic acid, and optionally a manganese-containing alloy, and subsequently subjecting the resultant reaction mixture to distillation.

12 Claims, No Drawings

METHOD FOR MANUFACTURE OF HIGH-PURITY PHTHALIC ANHYDRIDE

BACKGROUND OF THE INVENTION

1. Field of the Invention

This invention relates to a method for the manufacture of phthalic anhydride of high purity by refining crude phthalic anhydride obtained by vapor-phase catalytic oxidation of ortho-xylene. To be more particular, this invention relates to a method for the manufacture of high-purity phthalic anhydride by effecting efficient removal of such impurities as phthalide which are contained in the aforementioned crude phthalic anhydride and are difficult of separation therefrom.

2. Description of Prior Arts

Generally it is widely practiced to obtain phthalic anhydride by subjecting ortho-xylene, the raw material, to vapor-phase catalytic oxidation by use of a vanadium type catalyst. Into the crude phthalic anhydride obtained by this method contains impurities represented by by-produced phthalide. Such impurities cannot be sufficiently separated by distillation devices of the class ordinarily used commercially. Thus, refined phthalic anhydride has phthalide and other impurities persisting therein in hardly negligible amounts. It is well known that owing to these persistent impurities, the produced phthalic anhydride is liable to suffer from degradation of quality.

The process for the production of phthalic anhydride, therefore, requires the vapor-phase catalytic oxidation of ortho-xylene to be controlled so that the amount of phthalide suffered to occur as an impurity in the crude phthalic anhydride may be decreased to the fullest extent and retained at a low level. Generally it is inevitable, therefore, to elevate the reaction temperature for the purpose of curbing the decrease in the conversion of ortho-xylene and the increase in the amount of intermediate by-product phthalide due to a decline in the activity of the catalyst. This elevation of the reaction temperature results in a decrease in the service life of the catalyst. Even apart from this difficulty, the unwanted presence of by-produced phthalide in the crude phthalic anhydride is inevitable. In the commercial production of phthalic anhydride, various methods have been suggested for removal of the phthalide.

Japanese Patent Publication No. 10333/1970, for example, discloses a method which comprises treating the crude phthalic anhydride with a sulfur compound of alkali metal such as potassium hydrogen sulfite (KHSO$_3$) or potassium pyrosulfate (K$_2$S$_2$O$_5$) and U.S. Pat. No. 4,165,324 discloses a method which comprises effecting this treatment with an alkali metal hydroxide such as sodium hydroxide (NaOH) or potassium hydroxide (KOH). These methods, however, have been blamed for the following disadvantages, which are held to make their commercially beneficial adoption infeasible.

First, the former method has a disadvantage that since the residue originating in the refining step of phthalic anhydride contains a sulfur compound, a large amount of sulfur oxide occurs during the disposal (as by incineration, for example) of the residue and the sulur oxide induces the problem of air pollution, that the sulfur compound itself is liable to cause corrosion of the distillation device, and that a huge expense is required for the solution of these problems. Then, in the case of the latter method, since the reactivity of the alkali metal hydroxide itself is high, the treatment can become very dangerous depending on the particular type of crude phthalic anhydride to which the alkali metal hydroxide is to be added. When potassium hydroxide is added to crude phthalic anhydride in a liquid state, for example, maleic anhydride contained therein is explosively polymerized to form a polymer of the form of coke. This reaction is so violent as to have a hardly negligible effect upon the operation of the system used for the production of phthalic anhydride. Moreover, the resultant polymer of the form of coke can cause clogging in pipes, valves, and trays in the distillation tower. Further, the violent reaction of potassium hydroxide with maleic anhydride induces decomposition of phthalic anhydride and the impurities, with the result that the decomposition product reacts with phthalic anhydride to produce a polymer of the form of tar. The yield of refined phthalic anhydride, consequently, is heavily lowered.

Methods directed to obtaining phthalic anhydride of high purity by oxidizing phthalide with an oxidizing catalyst have also been proposed. U.S. Pat. No. 3,201,423, for example, discloses a method which comprises adding a heavy metal bromide such as cobalt bromide or manganese bromide to the crude phthalic anhydride and exposing the resultant mixture to contact with molecular oxygen gas. This method, however, is commercially infeasible because the bromide used in the catalyst is expensive and the recovery of the used catalyst for reuse is extremely difficult. For a similar purpose, West German Patent Disclosure No. 1,935,008 teaches a method which comprises forming a packed bed of catalyst having vanadium oxide deposited on a support and passing the crude phthalic anhydride through the packed bed while delivering air thereto thereby effecting oxidation of phthalide. It has been found, however, that when this method is adopted, the tarry substance present in the crude phthalic anhydride adheres to the surface of the supported catalyst and the catalyst is totally deprived of its activity in a very short time.

Generally, a support catalyst is formed by efficiently dispersing and depositing a catalytically active substance on the surface of a support. It is well known that even in accordance with this method of manufacture, the catalytic activity of the produced catalyst is largely affected such as by the burning condition. It is, therefore, only logical to conclude that any method which attempts to utilize such a supported catalyst placed in a packed column as a fixed bed will not be readily carried out stably on a commercial scale.

An object of this invention, therefore, is to provide a novel method for the manufacture of phthalic anhydride of high purity.

Another object of this invention is to provide a method for producing phthalic anhydride of high purity by effecting oxidation of phthalide by use of a catalyst which permits very easily controlled handling.

SUMMARY OF THE INVENTION

These objects of the present invention are accomplished by a method for the manufacture of phthalic anhydride of high purity, which comprises exposing crude phthalic anhydride obtained by vapor-phase catalytic oxidation of ortho-xylene to contact with a gas containing molecular oxygen at an elevated temperature in the presence of an alkali metal salt of at least one carboxylic acid selected from the group consisting of maleic acid, succinic acid and benzoic acid, and subsequently subjecting the resultant reaction system to distillation. This method yields better results when the aforementioned alkali metal salt is used in conjunction with a manganese-containing alloy composition.

PREFERRED EMBODIMENT OF THE INVENTION

Generally, the crude phthalic anhydride which is obtained by vapor-phase catalytic oxidation of orthoxylene contains phthalide as an impurity in an amount of 0.05 to 1.0% by weight. In a commercial operation, this crude phthalic anhydride is normally supplied in a molten state at 140° to 150° C. to the step of refining. It is then mixed with necessary chemical reagents, heated at temperatures of 150° to 300° C., and subsequently distilled.

In accordance with the present invention, refined phthalic anhydride containing substantially no phthalide can be obtained by a method which comprises adding to the crude phthalic anhydride containing phthalide as an impurity the alkali metal salt of at least one member selected from the group consisting of maleic acid, succinic acid, and benzoic acid, exposing the resultant mixture to contact with a gas containing molecular oxygen at temperatures of 150° C. to 300° C., preferably 200° C. to 300° C., for a period of 0.5 to 30 hours, preferably 1 to 20 hours thereby oxidizing the phthalide substantially completely, and thereafter subjecting the resultant system to distillation by an ordinary method. The molecular oxygen which is fed to the reaction system in this case is believed to function effectively, in conjunction with the alkali metal salt of carboxylic acid, as an oxidizing agent for the phthalide and compounds having near boiling temperatures (presumed to be aldehydes).

It has been ascertained that other organic acid salts than the aforementioned alkali metal salts of carboxylic acids, such as, for example, alkali metal salts of toluic acid, phthalic acid, and fumaric acid are invariably effective in decreasing phthalide to some extent but that their effectiveness is inferior to that of the aforementioned salts of carboxylic acids. What causes this difference is not known definitely but may be logically explained by a postulate that such other salts are inferior to those of the present invention in affinity for the reaction with phthalide such as, for example, oxidative activity.

The alkali metal salt of a carboxylic acid as involved in the present invention is a white crystalline substance obtained by the reaction of a corresponding carboxylic acid normally in an aqueous solution with an alkali metal hydroxide. It is an extremely stable compound. It has low explosiveness and flammability.

In the alkali metal salts of carboyxlic acids usable for this invention, examples of the alkali metals are sodium, potassium, lithium, cesium, and rubidium. Among other alkali metals, potassium proves to be particularly advantageous. Anong other carboxylic acids, maleic acid proves to be most desirable.

The amount in which the alkali metal salt of carboxylic acid is added to the reaction of the present invention, though variable with the amount of phthalide contained in the crude phthalic anhydride, generally falls in the range of 10 to 10,000 ppm (by weight), preferably 20 to 2,000 ppm (by weight), and more preferably 50 to 1,000 ppm (by weight) based on the crude phthalic anhydride under treatment.

The amount of the molecular oxygen to be fed to the reaction system, though variable with the amount of phthalide contained extraneously in the crude phthalic anhydride, is generally at least 0.0001 mole/hour, preferably at least 0.0005 mole/hour per kg of crude phthalic anhydride and more preferably in the range of 0.001 to 0.01 mole/hour per kg of crude phthalic anhydride. The manganese-containing alloy composition to be used in the present invention is desired to be obtained by weaving wires of the alloy in the shape of a net so that it may readily pass the gas containing molecular oxygen and cause practically no pressure loss. Particularly this invention can be most simply and conveniently carried out by a procedure which comprises piling such nets of the manganese-containing alloy composition in the form of a bed within a gas-liquid contact system, charging the system with the crude phthalic anhydride and the aforementioned alkali metal salt of carboxylic acid, and agitating and heating them with bubbles of molecular oxygen-containing gas generated in the lower part of the system and allowed to ascend the interior of the system.

The manganese-containing alloy composition to be used in the present invention is required to contain manganese in an amount of at least 0.05% by weight, preferably in the range of 0.1 to 10% by weight. Particularly in the alloy composition such as chromium-manganese alloy, iron-chromium-manganese alloy and iron-mium-manganese-nickel alloy which contain both manganese and chromium, the combined content of manganese and chromium is desired to be not less than 10% by weight. This alloy composition is advantageously used when it has a surface area of at least $1 \times 10^{-3}$ m$^2$, preferably at least $5 \times 10^{-3}$m$^2$, per kg of the crude phthalic anhydride under treatment. An increase in the surface area is desirable because it results in a reduction in the time required for the treatment. If the surface area is increased excessively, however, there ensues a disadvantage that pressure loss is increased.

It has been further ascertained that the combination of the alkali metal salt of carboxylic acid, the manganese-containing alloy composition, and oxygen is much more effective than the combination of the manganese-containing alloy composition and oxygen or the combination of the alkali metal salt of carboxylic acid and oxygen. It has been demonstrated that this three-member combination brings about a notable improvement in terms of time as well as temperature. What causes this conspicuous improvement is not known clearly but may be logically explained by a postulate that the alkali metal salt of carboxylic acid, the manganese-containing alloy composition, and the molecular oxygen produce some synergistic activity.

The distillation involved in this invention is performed, as normally practiced in this field of art, in the form of vacuum distillation. The degree of vacuum is generally 10 to 400 mmHg, preferably 20 to 200 mmHg.

This invention has been described in detail above. The advantages derived from this invention may be summarized as follows.

(A) The alkali metal salts of carboxylic acids contemplated for use in this invention are highly stable compounds having only low explosiveness and flammability. They have lower corrosiveness than potassium hydroxide.

(B) Since the salts of carboxlycic acids produce desired effects in small application rates, the amounts of such salts suffered to accumulate in the reaction system are also small. Further because they are readily soluble in the crude phthalic anhydride, they refrain from causing the phenomenon of clogging within the system and have no possibility of giving rise to polymers of the form of tar or coke. Thus, phthalic anhydride of high purity can be produced in high yields.

(C) The refining of phthalic anhydride is effected in improved yields by subjecting the crude phthalic anhydride to oxidation with molecular oxygen in the presence of the aforementioned alkali metal salt of carboxylic acid. This oxidation is believed to convert the phthalide extraneously contained in the crude phthalic anhydride into phthalic anhydride and, consequently, contribute to the improvement in the yield of refining. Besides the decrease in the content of phthalide, this oxidation is believed to bring about modification of compounds having near boiling temperatures and, consequently, facilitate isolation of phthalic anhydride from the extraneous components by distillation and enhance the quality of the produced phthalic anhydride.

(D) By the combined use of the alkali metal salt of carboxylic acid and the manganese-containing alloy composition, the phthalide content in the crude phthalic anhydride is decreased very quickly to 1/10 to 1/1000. Thus, the refined phthalic anhydride obtained after the final step of distillation enjoys high quality because the phthalide content is 0.01% by weight at most. It is surprising to note that the thermal stability of the phthalic anhydride which is obtained by the method of this is incomparably better than that of the product obtained by the conventional method.

Now, the present invention will be described more specifically below with reference to working examples of this invention and controls.

EXAMPLE 1

Crude phthalic anhydride obtained by vapor-phase catalytic oxidation of ortho-xylene has the following composition.

| | |
|---|---|
| Phthalic anhydride | 99.6% by weight |
| Benzoic acid | 0.05% by weight |
| Maleic acid | 0.07% by weight |
| Phthalic acid | 0.03% by weight |
| Phthalide | 0.20% by weight |

In a reaction vessel measuring 80 cm in inside diameter and 120 cm in height and provided therein with four baffle plates 8 cm in width, 500 kg of this crude phthalic anhydride was placed and heated at 275° C. This reaction vessel was provided in the lower portion thereof with a stirrer containing four fan turbine type blades having a size one third of the inside diameter of the vessel. Below this stirrer, a gas dispersing disc was set in position. To the reaction vessel, 50 g (equivalent to 100 ppm) of dipotassium maleate was added. The contents of the reaction vessel were stirred at 275° C. for 20 hours under continue upward introduction of a mixed gas consisting of 5% by volume of oxygen and the balance to make up 100% by volume of nitrogen through the bottom of the vessel at a flow volume of 1200 ml/hour.kg of phthalic anhydride (equivalent to 0.03 mole of oxygen hour.kg of phthalic anhydride). Then, the resultant reaction mixture was distilled under pressure of 55 mmHg (absolute pressure) at a reflux ratio of 0.5 in a distillation column (measuring 32 mm in inside diameter and 500 mm in height) provided with 10 stepped perforated boards, to afford refined phthalic anhydride having APHA 10 and a solidifying point of 131.12° C. This refined product had a phthalide content of less than 0.001% by weight and exhibited a thermal stability of APHA 20 after two hours' heating at 250° C. The yield of refining was 99.2% by weight. The interior of the reaction system was not found to retain any deposit of substance of the form of tar or coke.

CONTROL 1

The procedure of Example 1 was repeated, except that 50 g (equivalent to 100 ppm) of potassium hydroxide was used in the place of potassium maleate, to afford refined phthalic anhydride having APHA 15 and a solidifying point of 130.8° C. The phthalide content of this refined product was 0.13% by weight and the thermal stability thereof was APHA 90. The yield of refining was 98.1% by weight.

The stirrer's blades and the wall surface of the reaction vessel were found to retain a tarry deposit and the bottom of the distillation column was observed to retain a deposits of the form of coke. These deposite were responsible for the low yield of refining.

EXAMPLES 2–19 AND CONTROLS 2–3

In flasks, 1 kg aliquots of the same crude phthalic anhydride as used in Example 1 were placed and treated, with chemical reagents used for treatment, amounts of their addition, temperatures at time of their addition, temperatures of thermal treatment, and durations of thermal treatment varied as shown in Table 1. The phthalic anhydrides thus obtained were assayed for phthalide content. The results were as shown in Table 1.

TABLE 1

| Example | Chemical reagent used for treatment | Amount added (ppm) | Amount of oxygen (mole/hr · kg-PA) | Temperature (°C.) at addition | Temperature of treatment (°C.) | Duration of treatment (hr) | Phthalide content (% by weight) |
|---|---|---|---|---|---|---|---|
| 2 | dipotassium maleate | 1000 | $3 \times 10^{-3}$ | 270 | 270 | 15 | max. 0.001 |
| 3 | " | 100 | $3 \times 10^{-3}$ | 270 | 270 | 15 | 0.01 |
| 4 | " | 50 | $3 \times 10^{-3}$ | 270 | 270 | 15 | 0.08 |
| 5 | " | 100 | $6 \times 10^{-3}$ | 270 | 270 | 15 | 0.01 |
| 6 | " | 100 | $1.5 \times 10^{-3}$ | 270 | 270 | 15 | 0.06 |
| 7 | " | 100 | $3 \times 10^{-3}$ | 250 | 250 | 15 | 0.02 |
| 8 | " | 100 | $3 \times 10^{-3}$ | 280 | 280 | 15 | max. 0.001 |
| 9 | " | 100 | $3 \times 10^{-3}$ | 270 | 270 | 15 | 0.04 |
| 10 | " | 100 | $3 \times 10^{-3}$ | 270 | 270 | 20 | max. 0.001 |
| 11 | monopotassium maleate | 100 | $3 \times 10^{-3}$ | 270 | 270 | 15 | 0.01 |
| 12 | potassium benzoate | 100 | $3 \times 10^{-3}$ | 270 | 270 | 15 | 0.02 |
| 13 | dipotassium succinate | 100 | $3 \times 10^{-3}$ | 270 | 270 | 15 | 0.04 |
| 14 | dipotassium maleate dipotassium phthalate | 50 100 | $3 \times 10^{-3}$ | 270 | 270 | 15 | 0.07 |

TABLE 1-continued

| Example | Chemical reagent used for treatment | Amount added (ppm) | Amount of oxygen (mole/hr · kg-PA) | Temperature (°C.) at addition | Temperature of treatment (°C.) | Duration of treatment (hr) | Phthalide content (% by weight) |
|---|---|---|---|---|---|---|---|
| 15 | dipotassium maleate | 50 | $3 \times 10^{-3}$ | 270 | 270 | 15 | 0.06 |
|  | dipotassium-tumalate | 100 |  |  |  |  |  |
| 16 | monosodium maleate | 100 | $3 \times 10^{-3}$ | 270 | 270 | 15 | 0.05 |
| 17 | disodium maleate | 100 | $3 \times 10^{-3}$ | 270 | 270 | 15 | 0.07 |
| 18 | sodium benzoate | 100 | $3 \times 10^{-3}$ | 270 | 270 | 15 | 0.08 |
| 19 | monolithium maleate | 100 | $3 \times 10^{-3}$ | 270 | 270 | 15 | 0.08 |
| Control |  |  |  |  |  |  |  |
| 2 | potassium hydroxide | 1000 | $3 \times 10^{-3}$ | 270 | 270 | 15 | 0.18 |
| 3 | sodium hydroxide | 1000 | $3 \times 10^{-3}$ | 270 | 270 | 15 | 0.19 |

*PA: crude phthalic anhydride

EXAMPLE 20

Crude phthalic anhydride of the following composition was obtained by subjecting ortho-xylene to vapor-phase catalytic oxidation.

| Phthalic anhydride | 99.3% by weight |
|---|---|
| Benzoic acid | 0.05% by weight |
| Maleic acid | 0.07% by weight |
| Phthalic acid | 0.03% by weight |
| Phthalide | 0.50% by weight |

In a flask, 1 kg of the crude phthalic anhydride and 0.1 g (equivalent to 100 ppm) of potassium maleate were placed and treated at a temperature of 270° C. for 10 hours, with a mixed gas consisting of 5% by volume of oxygen and 95% by volume of nitrogen introduced upwardly from the bottom at a rate of 3,000 ml/hour ($6 \times 10^{-3}$ mole/hour.kg of phthalic anhydride). In the flask, 20 g of a wire of iron-chromium-manganese alloy having the following composition and constitution was coiled in the shape of a circular plate and set in position in advance of the treatment.

The composition and constitution of the iron-chromium-manganese alloy were as follows.

| Iron | about 70% by weight |
|---|---|
| Chromium | about 19% by weight |
| Manganese | about 0.2% by weight |
| Nickel | about 9% by weight |
| Specific surface area | 156 m²/m³ |
| Void ratio | 99% |
| Density | 80 kg/m³ |

The phthalic anhydride obtained at the end of the treatment had a phthalide content of 0.01% by weight. In a distillation column (measuring 32 mm in inside diameter and 500 mm in height) provided with 10 stepped perforated boards, the phthalic anhydride issuing from the treatment was distilled under pressure of 55 mmHg (absolute pressure) and a reflux ratio of 0.5. Consequently, there was obtained refined phthlacic anhydride having APHA 10 and a solidifying point of 131.12° C.

After two hours of heating at 250° C., the refined phthalic anhydride retained a thermal stability of APHA 10. This refined phthalic anhydride had a phthalide content of 0.008% by weight.

EXAMPLE 21

In a flask, 1 kg of the same crude phthalic anhydride as used in Example 20 and 0.2 g (equivalent to 200 ppm) of potassium benzoate were placed and treated at a temperature of 280° C. for five hours by continued upward introduction of a mixed gas consisting of 5% by volume of oxygen and 95% by volume of nitrogen from the bottom at a flow volume of 4,500 ml/hour ($9.4 \times 10^{-3}$ mole/hour.kg of phthalic anhydride of oxygen). In the flask, 5 g (equivalent to $75 \times 10^{-3}$ m² of contact area of wire of iron-chromium-manganese having the following composition and constitution was placed in advance of the treatment.

| Iron | about 69% by weight |
|---|---|
| Chromium | about 17% by weight |
| Manganese | about 9% by weight |
| Nickel | about 5% by weight |
| Surface area | 1515 m²/m³ |
| Void ratio | 98.2% |
| Density | 100 kg/m³ |

The phthalic anhydride obtained by this treatment had a phthalide content of 0.005% by weight. In a distillation column (measuring 32 mm in inside diameter and 500 mm in height) provided with 10 stepped perforated boards, the phthalic anhydride thus obtained was distilled under pressure of 55 mmHg (absolute pressure) at a reflux ratio of 0.5. Consequently, there was obtained refined phthalic anhydride having APHA 10 and a solidifying point of 131.12° C.

Even after two hours' heating at 250° C., the thermal stability was APHA 10. This refined phthalic anhydride has a phthalide content of 0.003% by weight.

EXAMPLE 22

In a vertical treating vessel 80 cm in inside diameter and 120 cm in height, 500 kg of the same crude phthalic anhydride as used in Example 20 was placed. The vessel was provided on the bottom thereof with a dispersion disc for delivery of a mixed gas consisting of 5% by volume of oxygen and 95% by volume of nitrogen. Above this disc was provided a stirrer. In the middle-step portion of this treating vessel, 1250 g of a net of chromium-manganese alloy wires (equivalent to $10 \times 10^{-3}$ M² of contact rear per kg of phthalic anhydride) having the following composition and constitution was placed in advance of the treatment.

| Iron | about 88% by weight |
|---|---|
| Chromium | about 11% by weight |
| Manganese | about 1% by weight |
| Surface area | 1780 m²/m³ |
| Void ratio | 94.5% |
| Density | 430 kg/m³ |

To the vessel, 25 g (equivalent to 50 ppm) of potassium succinate was added. Thereafter, the contents of the vessel were treated at 275° C. for 15 hours by continued introduction of the mixed gas at a flow volume of 840 liters/hour (equivalent to $3.5 \times 10^{-3}$ mole/hour.kg of phthalic anhydride of oxygen). After this treatment the resultant reaction mixture was distilled under pressure of 55 mmHg (absolute pressure) at a reflux ratio of 0.5 in a distillation column (measuring 3.2 cm in inside diameter and 50 cm in height) provided with 10 stepped perforated boards. Consequently, there was obtained high-purity phthalic anhydride having APHA 10, a solidifying point of 131.11° C., and a phthalide content of 0.05% by wegiht. After two hours of heating at 250° C., the thermal stability of the phthalic anhydride was APHA 20.

EXAMPLE 23

A vertical treating vessel measuring 80 cm in inside diameter and 120 cm in height was charged with 500 kg of the same crude phthalic anhydride as used in Example 20. On the bottom of this vessel was provided a dispersion disc for delivery of gas. Above this disc was provided a stirrer. In the middle-step portion of this vessel was disposed 300 g of a net of chronium-manganese alloy wires ($2.7 \times 10^{-3}$ m$^2$ of contact area per kg of phthalic anhydride) having the following composition and constitution.

| | |
|---|---|
| Iron | about 68% by weight |
| Chromium | about 20% by weight |
| Manganese | about 2% by weight |
| Nickel | about 10% by weight |
| Surface area | 900 m$^2$/m$^3$ |
| Void ratio | 94.5% |
| Density | 200 kg/m$^3$ |

To the vessel, 150 g (equivalent to 300 ppm) of sodium succinate was added. Thereafter, the contents of the vessel were treated at 265° C. for 12 hours by continued introduction of a mixed gas consisting of 5% by volume of oxygen and 95% by volume of nitrogen at a flow volume of 1200 liters/hour (equivalent to $5 \times 10^{-3}$ mole/hour of oxygen per kg of phthalic anhydride). Then, in a distillation column (measuring 3.2 cm in inside diameter and 50 cm in height) provided with 10 stepped perforated boards, the resultant reaction mixture was distilled under pressure of 55 mmHg (absolute pressure) at a reflux ratio of 0.5. Consequently, there was obtained high-purity phthalic anhydride having APHA 10, a solidifying point of 131.12° C., and a phthalide content of 0.01% by weight. After two hours of heating at 250° C., this product had thermal stability of APHA 20.

CONTROL 4

When the procedure of Example 20 was repeated, except that the addition of potassium maleate and the chromium-manganese alloy composition was omitted, the produced phthalic anhydride had APHA 50, colored in yellow. It has a solidifying point of 130.5° C. This phthalic anhydride has a phthalide content of 0.48% by weight. After two hours of heating at 250° C., the thermal stability was over APHA 500.

EXAMPLES 24-44 AND CONTROLS 5-6

The procedure of Example 23 was repeated, except that the kind of additives, the amount of their addition, the amount of manganese alloy composition used, the contact surface of the composition, the amount of oxygen supplied, the temperature at addition, the temperature of treatment, and the duration of treatment varied as shown in Table 2. The phthalic anhydrides thus produced were assayed for phthalide content. The results were as shown in Table 2.

TABLE 2

| Example | Treating agent | Amount added (ppm) | Alloy Amount used (g) | Alloy Contact area (m$^2$) | Amount of oxygen (mol/hr · kg-PA) | Refining Temperature at addition (°C.) | Refining Temperature of treatment (°C.) | Duration of treatment (hr) | Phthalide content (% by weight) |
|---|---|---|---|---|---|---|---|---|---|
| 24 | dipotassium maleate | 1000 | 10 | $4.5 \times 10^{-2}$ | $6 \times 10^{-3}$ | 270 | 270 | 10 | max. 0.001 |
| 25 | " | 100 | 10 | $4.5 \times 10^{-2}$ | $6 \times 10^{-3}$ | 270 | 270 | 10 | 0.01 |
| 26 | " | 10 | 10 | $4.5 \times 10^{-2}$ | $6 \times 10^{-3}$ | 270 | 270 | 10 | 0.12 |
| 27 | " | 100 | 500 | | $6 \times 10^{-3}$ | 270 | 270 | 10 | 0.01 |
| 28 | " | 100 | 50 | $225 \times 10^{-2}$ | $6 \times 10^{-3}$ | 270 | 270 | 10 | 0.01 |
| 29 | " | 100 | 1 | $22.5 \times 10^{-2}$ | $6 \times 10^{-3}$ | 270 | 270 | 10 | 0.05 |
| 30 | " | 100 | 10 | $4.5 \times 10^{-2}$ | $40 \times 10^{-3}$ | 270 | 270 | 10 | 0.01 |
| 31 | " | 100 | 10 | $4.5 \times 10^{-2}$ | $15 \times 10^{-3}$ | 270 | 270 | 10 | 0.01 |
| 32 | " | 100 | 10 | $4.5 \times 10^{-2}$ | $2 \times 10^{-3}$ | 270 | 270 | 10 | 0.08 |
| 33 | " | 100 | 10 | $4.5 \times 10^{-2}$ | $6 \times 10^{-3}$ | 250 | 250 | 10 | 0.09 |
| 34 | " | 100 | 10 | $4.5 \times 10^{-2}$ | $6 \times 10^{-3}$ | 280 | 280 | 10 | max. 0.001 |
| 35 | " | 100 | 10 | $4.5 \times 10^{-2}$ | $15 \times 10^{-3}$ | 270 | 270 | 5 | 0.09 |
| 36 | " | 100 | 10 | $4.5 \times 10^{-2}$ | $3 \times 10^{-3}$ | 270 | 270 | 15 | max. 0.001 |
| 37 | " | 4000 | 10 | $4.5 \times 10^{-2}$ | $80 \times 10^{-3}$ | 270 | 270 | 0.5 | max. 0.001 |
| 38 | monopotassium maleate | 100 | 10 | $4.5 \times 10^{-2}$ | $6 \times 10^{-3}$ | 270 | 270 | 10 | 0.01 |
| 39 | potassium benzoate | 100 | 10 | $4.5 \times 10^{-2}$ | $6 \times 10^{-3}$ | 270 | 270 | 10 | 0.03 |
| 40 | potassium succinate | 100 | 10 | $4.5 \times 10^{-2}$ | $6 \times 10^{-3}$ | 270 | 270 | 10 | 0.04 |
| 41 | monosodium maleate | 100 | 10 | $4.5 \times 10^{-2}$ | $3 \times 10^{-3}$ | 270 | 270 | 20 | 0.07 |
| 42 | disodium maleate | 100 | 10 | $4.5 \times 10^{-2}$ | $3 \times 10^{-3}$ | 270 | 270 | 20 | 0.07 |
| 43 | sodium benzoate | 100 | 10 | $4.5 \times 10^{-2}$ | $3 \times 10^{-3}$ | 270 | 270 | 20 | 0.08 |
| 44 | sodium succinate | 100 | 10 | $4.5 \times 10^{-2}$ | $3 \times 10^{-3}$ | 270 | 270 | 20 | 0.03 |
| Control 5 | potassium phthalate | 100 | 10 | $4.5 \times 10^{-2}$ | $6 \times 10^{-3}$ | 270 | 270 | 20 | 0.25 |
| Control 6 | potassium fumarate | 100 | 10 | $4.5 \times 10^{-2}$ | $6 \times 10^{-3}$ | 270 | 270 | 20 | 0.28 |

*PA: crude phthalic anhydride

What is claimed is:

1. A method for the manufacture of high-purity phthalic anhydride, which comprises exposing crude phthalic anhydride obtained by vapor-phase catalytic oxidation of ortho-xylene to contact with, per Kg of crude phthalic anhydride, a gas containing molecular oxygen at a rate of at least 0.0001 mole/hour of oxygen, at an elevated temperature in the presence of 10–10,000 ppm by weight, as alkali metal atom, of an alkali metal salt of at least one carboxylic acid selected from the group consisting of maleic acid, succinic acid and benzoic acid, and subsequently subjecting the resultant reaction mixture to distillation.

2. A method according to claim 1, wherein the contact treatment is carried out at temperatures in the range of 150° C. to 300° C. for a period of 0.5 to 30 hours.

3. A method according to claim 2, wherein the amount of the alkali metal salt of carboxylic acid to be used is in the range of 20 to 2,000 ppm (by weight) of alkali metal atom based on the crude phthalic anhydride.

4. A method according to claim 1, wherein the crude phthlaic anhydride is brought into contact with molecular oxygen containing gas at a rate of at least 0.0005 mole/hour as oxygen gas per kg of said crude phthalic anhydride.

5. A method according to claim 1, wherein the alkali metal is potassium.

6. A method for the manufacture of high-purity phthalic anhydride, which comprises exposing crude phthalic anhydride obtained by vapor-phase catalytic oxidation of ortho-xylene, par Kg thereof, to contact with a gas containing at least 0.0001 mole/hour of molecular oxygen at an elevated temperature in the presence of 10–10,000 ppm by weight, as alkali metal atom of an alkali metal salt of at least one carboxylic acid selected from the group consisting of maleic acid, succinic acid and benzoic acid together with a manganese-containing alloy composition, of at least 0.05% by weight and a surface area of at least $5 \times 10^3 m^2$ and subsequently subjecting the resultant reaction mixture to distillation.

7. A method according to claim 6, wherein the contact treatment is carried out at temperatures in the range of 150° C. to 300° C. for a period of 0.5 to 30 hours.

8. A method according to claim 7, wherein the amount of the alkali metal salt of carboxylic acid to be used is in the range of 20 to 20,000 ppm (by weight) as alkali metal atom based on the crude phthalic anhydride.

9. A method according to claim 6, wherein the crude phthalic anhydride is brought into contact with the molecular oxygen-containing gas at a rate of at least 0.0005 mole/hour as oxygen gas per kg of said crude phthalic anhydride.

10. A method according to claim 6, wherein the contact area of the manganese-containing alloy composition is at least $5 \times 10^{-3} m^2$ per kg of the crude phthalic anhydride.

11. A method according to claim 6, wherein the manganese content of the manganese-containing alloy is in the range of 0.1 to 10% by weight.

12. A method according to claim 6, wherein the manganese-containing alloy composition is an alloy containing manganese and chromium in a combined amount of not less than 101% by weight.

* * * * *